(12) United States Patent
Soss et al.

(10) Patent No.: US 6,673,117 B1
(45) Date of Patent: Jan. 6, 2004

(54) SINGLE AXIS KNEE JOINT ASSEMBLY

(76) Inventors: Adam Soss, 1504 Laurie Rd., St. Paul, MN (US) 55109; David F. Ackley, 31785 Frontier Ave., Stacy, MN (US) 55079

( * ) Notice: Subject to any disclaimer, the term of this patent is extended or adjusted under 35 U.S.C. 154(b) by 42 days.

(21) Appl. No.: 10/002,099

(22) Filed: Nov. 28, 2001

Related U.S. Application Data

(60) Provisional application No. 60/250,226, filed on Nov. 30, 2000.

(51) Int. Cl.$^7$ ................................................ A61F 2/48
(52) U.S. Cl. ............................................ 623/24; 623/46
(58) Field of Search ......................... 623/24–27, 32–37, 623/39, 40, 42–46

(56) References Cited

U.S. PATENT DOCUMENTS

| | | | |
|---|---|---|---|
| 4,662,486 A | | 5/1987 | Stenberg |
| 4,775,037 A | | 10/1988 | Stenberg |
| 5,571,205 A | * | 11/1996 | James ........................ 623/24 |
| 6,106,560 A | * | 8/2000 | Boender ...................... 623/24 |
| 6,113,642 A | * | 9/2000 | Petrofsky et al. .............. 623/24 |
| 6,517,585 B1 | * | 2/2003 | Zahedi et al. ................. 623/24 |
| 6,558,430 B1 | * | 5/2003 | Nakaya et al. ................ 623/24 |

* cited by examiner

*Primary Examiner*—David H. Willse
*Assistant Examiner*—Javier G. Blanco
(74) *Attorney, Agent, or Firm*—D L Tschida

(57) ABSTRACT

A prosthetic leg having a knee joint assembly that includes a plunger-activated, three-chamber cylinder body, a control valve, a control valve actuator, a pylon shaft and artificial foot. The knee joint assembly rotates in a single axis and provides two-stage hydraulic gait control and shock absorption relative to two spring-biased pistons. A cam linkage and actuator valve having a moveable piston and piston chamber responds to knee flexion and switches fluid flow at the control valve and cylinder between a "soft" spring and a "hard" spring to provide two levels of adjustable control to stabilize the user. Alternative microprocessor directed electronic and hydraulic controllers are also disclosed that can be adapted to a knee assembly to sense myoelectric activity and rotation, strain, and/or linear movement of the prosthesis.

20 Claims, 9 Drawing Sheets

SINGLE AXIS KNEE JOINT ASSEMBLY

RELATED APPLICATIONS

This application claims the benefit of U.S. provisional application ser. No. 60/250,226 filed on Nov. 30, 2000.

BACKGROUND OF THE INVENTION

The invention relates to a prosthetic knee assembly that pivots in a single axis, and in particular to a knee assembly having a two-stage, weight activated hydraulic valve body and linkage that accommodates normal gait and also stabilizes the knee against shock and/or during strenuous or other movement requiring knee flexion.

Prior art hydraulic prosthetic knee assemblies have typically utilized a single valve chamber. The assemblies allow the knee to pivot freely when raised during normal gait. When loaded with the user's weight, the single chamber controls the gait speed (i.e. leg swing) and partially dampens the relatively soft walking forces. Gait control hydraulic assemblies are shown at U.S. Pat. Nos. 4,775,037 and 4,662,486 that provide duplex movement of a pair of pistons in two cylinders.

The prior art devices, however, limit the physical activities of the user. They are particularly not designed to accommodate physical activities requiring leg/knee flexion, such as during stair transitions or encountered in many physical sports, for example skiing, snowboarding, skateboarding, volleyball or other sports where high stress forces are periodically encountered during landings. An improved assembly is therefore desired to provide greater knee stability and accommodate more active lifestyles.

The present prosthetic knee assembly includes a socket, harness or other suitable mechanism to attach to the user. A pylon and suitable prosthetic foot depend from the prosthetic knee assembly. An intermediate pivot joint and two-stage hydraulic shock member and cooperating linkage stabilize the knee during flexion and accommodate both soft and hard shock loads.

The prosthetic knee of the present invention provides an assembly that includes a two stage hydraulic cylinder. Cylinder operation is controlled by a linkage that translates relative upward forces exerted on the foot and the rotation of the knee joint to direct hydraulic flow and piston action at the available stages. One stage provides an adjustable rebound force or extension assistance that offsets the user's normal gait pattern. That is, the knee pivots freely, when raised, and a first piston biased by an adjustable soft spring directs fluid flow to provide sufficient force to control gait speed and partially offset the user's weight when the foot contacts the ground. The second stage includes a second piston biased by a spring with a heavier weight spring that is activated by knee flexion and provides a relatively greater offsetting force to stabilize knee rotation, such as during stair transitions, when landing from jumps or encountering other shock loads. The user is thereby provided greater stability for activities requiring knee flexion under load conditions and is able to engage in a wider range of physical activities, such as skiing and other sports that stress the legs.

SUMMARY OF THE INVENTION

It is accordingly a primary object of the invention to provide a prosthetic knee capable of providing several different levels of reactionary or offsetting support forces relative to physical activity to maintain user stability, for example, gait control and shock absorption.

It is a further object of the invention to provide a prosthetic knee support control having several stages that offer several adjustable ranges of reactionary or offsetting support forces.

It is a further object of the invention to provide a prosthetic knee having an adjustable two-stage hydraulic control wherein a first stage responds with approximately 50 to 100 lbs. of support for light duty activities and a second stage responds with approximately 250 to 600 lbs. of support for more strenuous activities, such as stair transitions, skiing, snowboarding.

It is a further object of the invention to provide a prosthetic knee with a hydraulic control wherein a cam-actuated linkage, upon experiencing knee flexion or rotation in excess of 5 degrees of rotation, switches fluid flow relative to first and second spring biased pistons.

It is a further object of the invention to provide an actuator body that responds to load forces at the leg to pre-set a piston and moveable piston chamber to respond to enhanced loading and re-direct flow within a multi-chambered cylinder.

The foregoing and other objects, advantages and distinctions of the invention are obtained in a prosthetic leg assembly having a suction socket, prosthetic foot, pylon and improved prosthetic knee. A single-axis knee joint assembly includes a plunger-activated, three-chamber cylinder body, a control valve body, a control valve actuator, a pylon shaft and artificial foot.

The knee joint assembly rotates in a single axis and provides a two-stage hydraulic gait control and shock absorption system that is activated by the weight of the wearer during use. The load forces on the knee cause a plunger to travel in a first cylinder and direct fluid flow as determined by control and actuator valve bodies to selectively pass through second and/or third cylinders containing spring biased pistons. Hydraulic fluid is directed to pass to either a second cylinder containing a "soft" spring and/or into a third cylinder containing a "hard" spring, depending upon the force exerted on the activator body by the pylon shaft and flexion experienced by the knee. Two different levels of adjustable shock absorption or offsetting forces are applied in response to stabilize the user. Adjustment controls are provided at the soft and hard spring cylinders and control valve body. The actuator valve body includes a floating piston and piston chamber.

Alternative microprocessor directed electronic and hydraulic controllers are disclosed that can be adapted to a knee assembly to sense myoelectric activity and physical movement at the prosthesis, such as rotation, strain, and/or linear movement and appropriately stabilize joint movement.

These and other benefits, advantages, distinctions and constructions of the invention will become more apparent from the following description with respect to the appended drawings. Similar components and assemblies are referred to in the various drawings with similar alphanumeric reference characters. The description should not be literally construed in limitation of the invention. Rather, the invention should be interpreted within the broad scope of the further appended claims.

DESCRIPTION OF THE PREFERRED EMBODIMENTS

Figure 1:
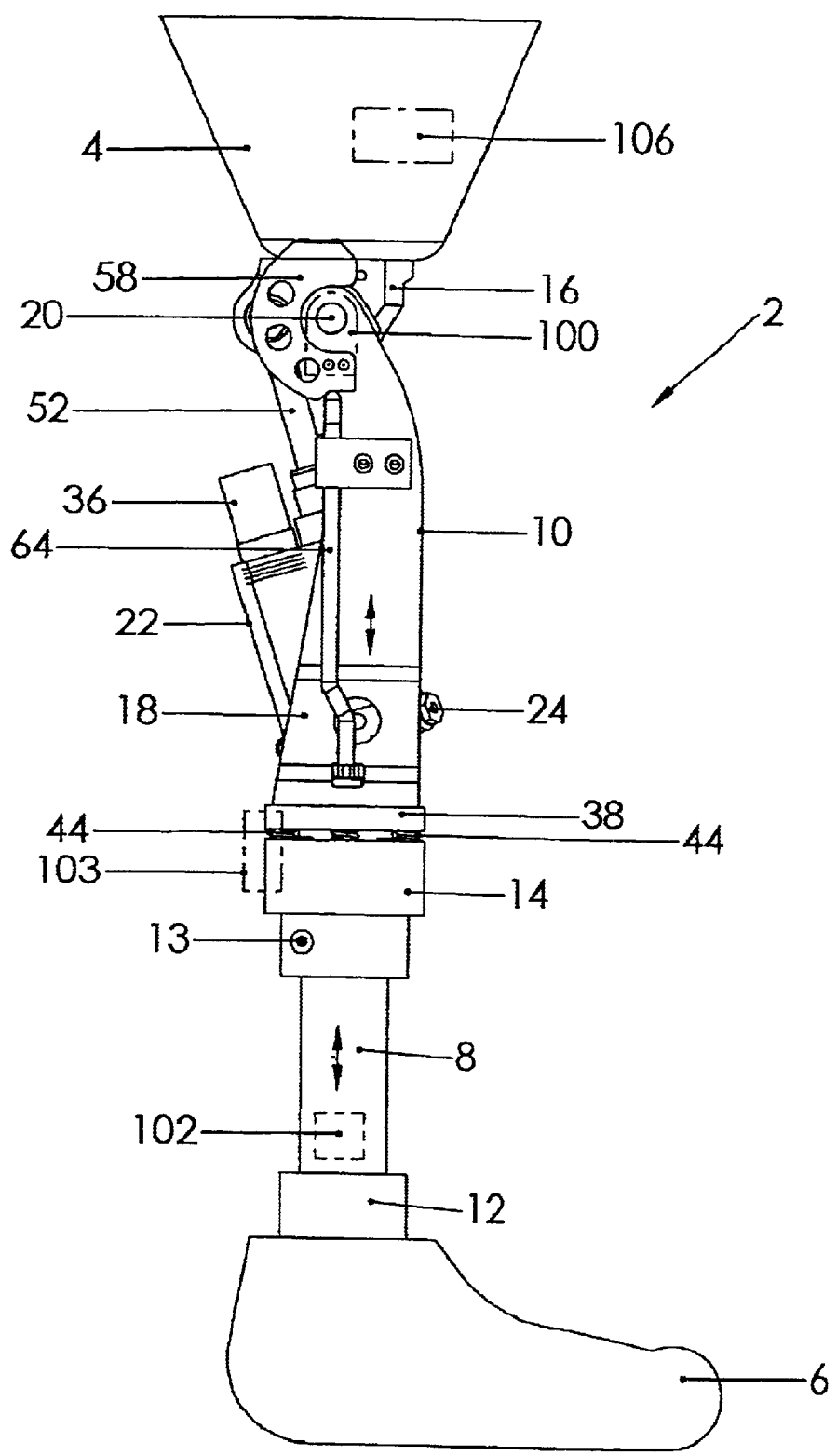
FIG. 1 is a plan view of a prosthetic leg assembly including the hydraulic, single axis knee joint assembly of the invention.
Figure 2:
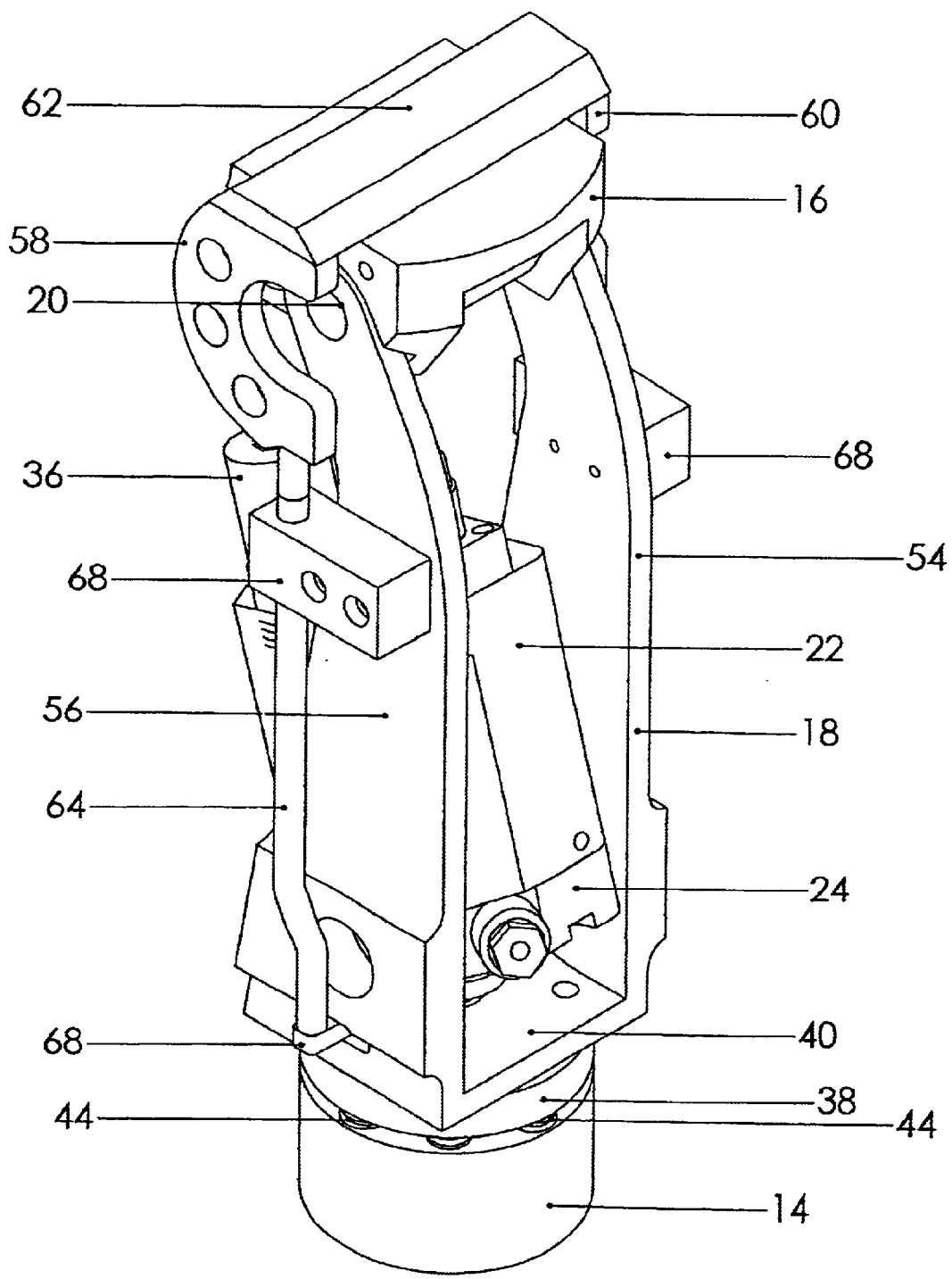
FIG. 2 is an isometric view of the control valve and cylinder bodies and interconnecting linkage of the knee joint assembly of FIG. 1.

Referring to FIGS. 1 and 2, a prosthetic leg assembly 2 is shown that includes a suction socket 4, a prosthetic foot 6, a pylon 8 and a two-stage, single axis knee joint assembly 10 of the present invention. The foot 6 and pylon 8 attach to each other at a coupler 12 that can be adjusted to provide a preferred alignment. The upper end of the pylon 8 is secured to the knee assembly 10 at a control valve actuator body 14 with a number of setscrews 13. The setscrews 13 prevent the pylon 8 from rotating relative to the knee assembly 10.

The suction socket 4 is shaped and constructed to secure the leg assembly 2 to the user at a stump piece of the amputated limb. Depending upon the available stump, a variety of types and styles of conventional sockets 4, harnesses, straps, splints etc. can be adapted to provide a secure connection. A variety of types and styles of feet 6, pylons 8 and couplers 12 are similarly available that can be coupled to the knee assembly 10 to accommodate different user preferences and activities.

Mounted between the pylon 8 and socket 4 is the knee assembly 10 and which is generally constructed of an upper yoke 16 and a lower yoke 18 that are secured together at a pivot axle 20. The yokes 16 and 18 are free to rotate about the axle 20 relative to compensating forces obtained from a two-stage hydraulic cylinder body 22 and control valve body 24 that are mounted to the lower yoke 18 and which are respectively shown in greater detail at FIGS. 3 through 5 and 6 and 7.

Figure 3:
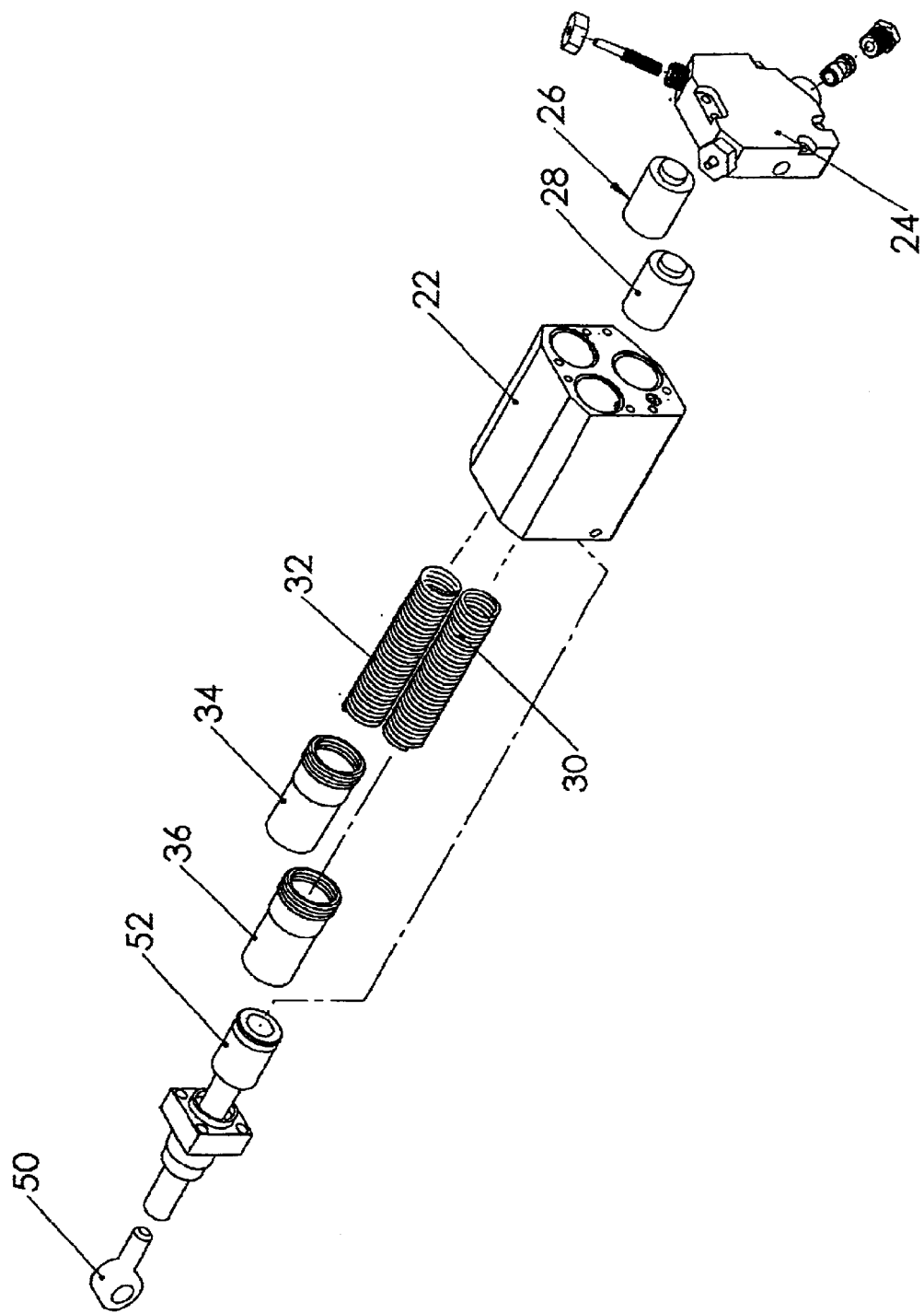
FIG. 3 is an isometric view of the control valve and cylinder body shown in exploded assembly.

Cooperating mechanical and hydraulic linkages coupled to the yokes 16 and 18 particularly respond to leg movement and leg loading to appropriately direct fluid flow relative to a pair of spring biased pistons 26 and 28 in the cylinder body 22 that store energy and/or act to counter balance encountered forces, reference FIG. 3. The first stage piston 28 of the cylinder body 22 stabilizes gait control and provides a relatively "soft" offsetting or rebound force during walking and low stress conditions. A relatively harder offsetting force is applied by the second stage piston 26 during higher stress conditions, especially when the knee 10 experiences flexion or rotation such as when traversing stairs, landing from a jump or pedaling a bike.

A "soft" spring 30 and a "hard" spring 32 determine the magnitude of the support force. The "soft" spring 30 presently exhibits a spring constant in the range of 50 to 100 lbs. of support for light duty activities and the "hard" spring 32 exhibits a spring constant in the range of 250 to 600 lbs. to compensate for strenuous physical activity, such as skiing, snowboarding, bicycling, climbing etc. The amount of force can be adjusted with screw adjusters 30 and 32 that vary the pre-compression of the springs 34 and 36.

The control valve actuator body 14 and control valve 24 determine hydraulic control over cylinder operation. With additional attention to FIG. 8, a cap piece 38 of the control valve actuator body 14 is mounted to a base plate 40 of the lower support yoke 18. The actuator body 14 is secured to the cap piece 38 with a number of screws 42 and springs 44 to permit longitudinal movement relative to each other. An actuation piston 46 is contained in a moveable piston chamber 47 and cylinder 45 of the actuator body 14. The piston chamber 47 and piston 46 normally floats within the actuator body 14.

Placement of weight on the foot 6 causes the actuator body 14 to slide along the screws 42 and abut the cap piece 38. In this condition, the piston chamber 47 is positioned such that the actuation piston 46 can be engaged to direct fluid flow to a poppet valve 48 at the control valve body 24, reference FIGS. 6 and 7. Movement of the poppet valve 48 switches fluid flow between the first and second stage pistons 28 and 26.

During a normal walking action and as the leg 2 contacts the ground, the control valve actuator body 14 merely moves up and down and the piston chamber 47 and piston 46 float within the cylinder 45 of the actuator body 14. Fluid flow is directed by the plunger 52 and provided flow channels in the cylinder body 22 to the first stage piston 28 and soft spring 30 to compensate for the forces on the leg 2 while in contact with the ground. Leg swing or gait speed is particularly controlled or dampened, depending upon related adjustments at the adjuster 36 to the first stage and a needle valve 76 at the control valve 24, such as in the fashion of a hydraulic door closer. Otherwise, when the foot 2 is not in contact with the ground, the knee assembly 10 rotates freely at the axle 20.

During more strenuous activities requiring knee flexion, flow is directed to the second stage piston 26 to provide increased support to the knee assembly 10 while under load and flexion conditions. The counterbalancing force can be adjusted with the adjuster 34 at the second stage and a needle valve 74 at the control valve 24.

Figure 4:
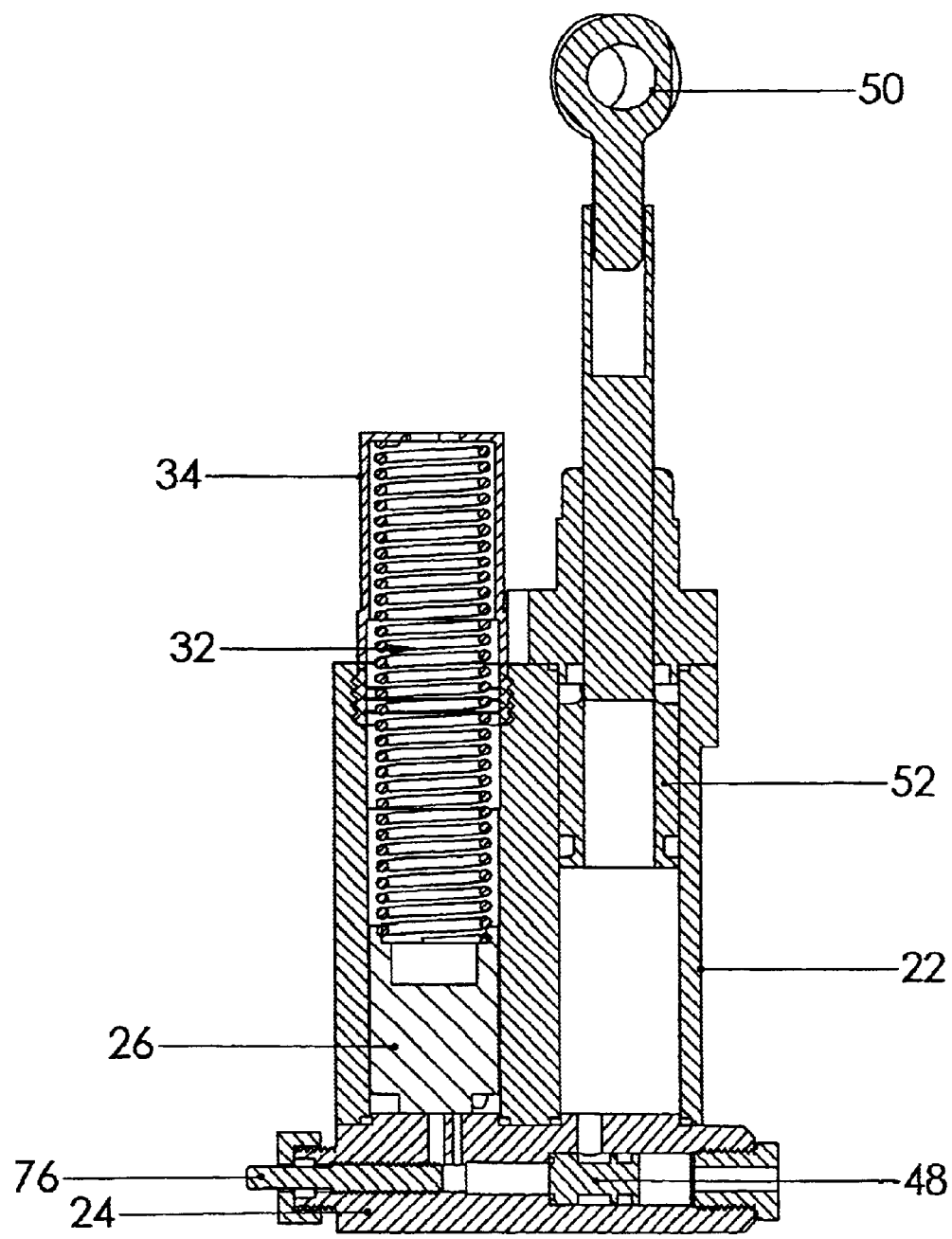
FIG. 4 is longitudinal cross section view through the control valve and cylinder bodies.
Figure 5:
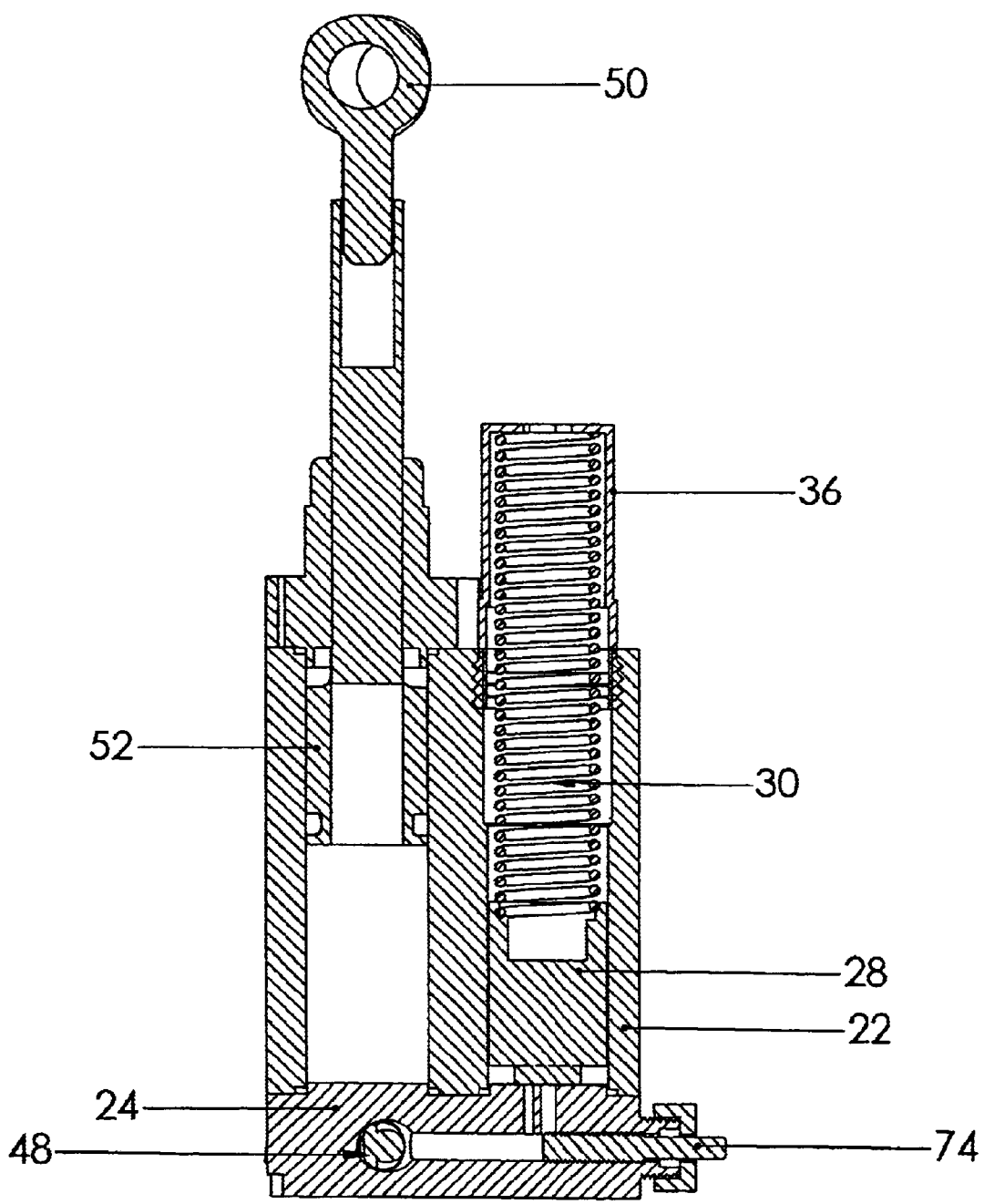
FIG. 5 is longitudinal cross section view through the control valve and cylinder bodies.
Figure 8:
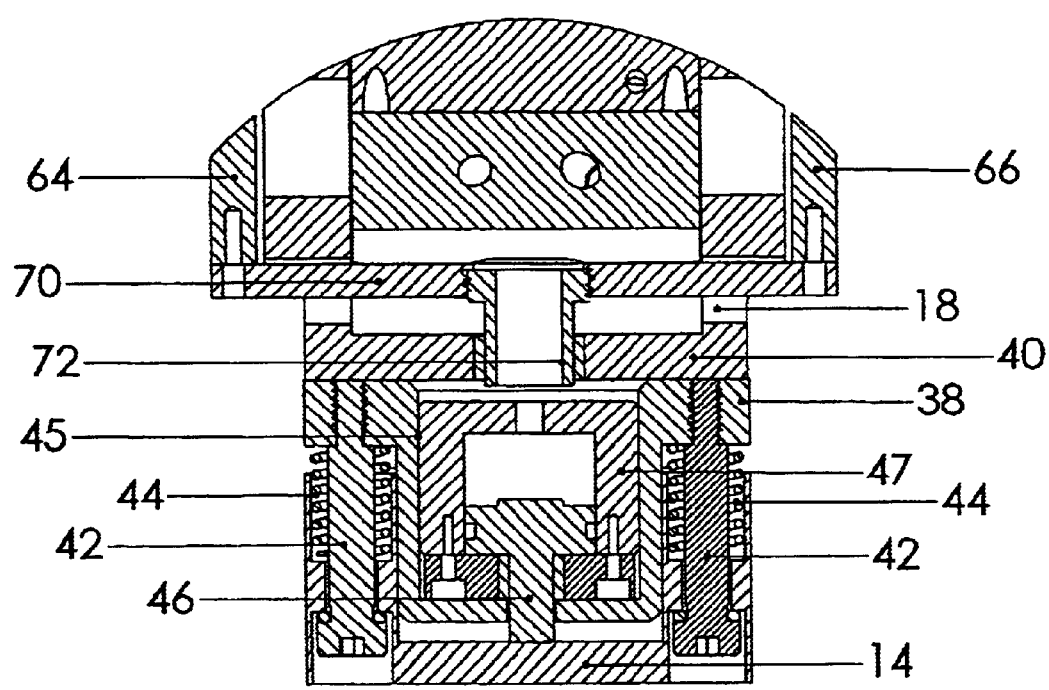
FIG. 8 is a cross section view through the control valve actuator body.

With continuing attention to FIG. 8 and additional attention to FIGS. 2, 4 and 5, the socket 4 attaches to the knee assembly 10 at the upper connection yoke 16. Laterally supported in the yoke 16 is the pivot axle 20 that extends through a collar 50 of a plunger valve or piston 52 and right and left arms 54 and 56 of the lower support yoke 18. The placement of weight on the foot 6 depresses the plunger valve 52. This movement is resisted by a selected one of the pistons 26 and 28, depending upon the fluid coupling with the cylinder body 22. The magnitude of resistance is determined by the springs 30 and 32. The control valve body 24 establishes the fluid flow path that selects the piston and resistance as determined by the position of the poppet valve 48 and the piston chamber 47 and actuation piston 46 in the control valve actuator 14.

The actuation piston 46 is controlled by the action of flexion cams 58 and 60 that are secured to the yoke 16 with a cross plate 62. The cams 58 and 60 rotate with the yoke 16 as the knee 10 flexes or rotates. Under high stress conditions and with rotational movement of the yoke 16, the cams 58 and 60 induce a longitudinal movement of push rods 64 and 66. The range of cam movement can set as desired in the nominal range of 5° to 15°, although the cams 58 and 60 are presently set to operate at 9° to 10°.

The push rods 64 and 66 are mounted to slide bearings 68 at the sides of the yoke arms 64 and 66 to direct an end piece 70, trained between the push rods 64 and 66, and a depending hollow, pushpin 72. The pushpin 72 extends through the cap piece 38 and into the cylinder 45 of the control valve actuator body 24. Knee rotation in excess of 9° causes the pushpin 72 to contact the piston chamber 47.

Simultaneous placement of a load on the pylon 8 elevates the actuation piston 46 (i.e. active state) and diverts fluid from the chamber 47 and control valve actuator body 14 via a conduit (not shown) to the control valve body 24 to direct movement of the poppet valve 48. A short length of tubing is presently coupled between the actuator body 14 and control valve body 24, although ported channels can be provided. During the active state, the poppet valve 48 is directed to block flow to the first stage piston 28 and shift the flow to the second stage piston 26, which provides an increased resistance to knee movement.

Figure 6:
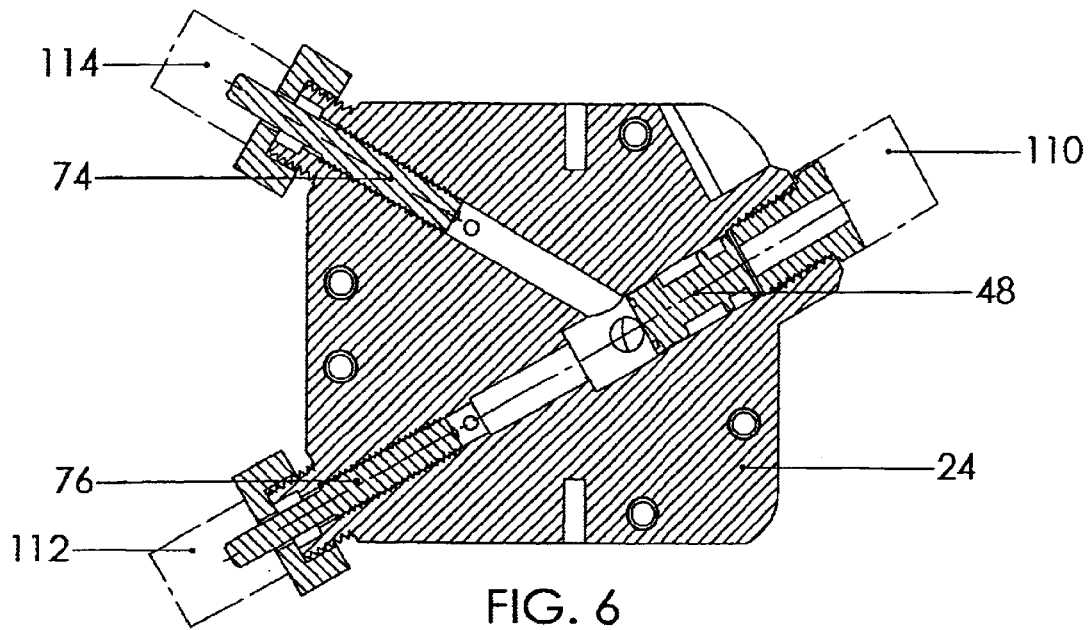
FIG. 6 is a cross section view through the control valve body in an inactive condition.
Figure 7:
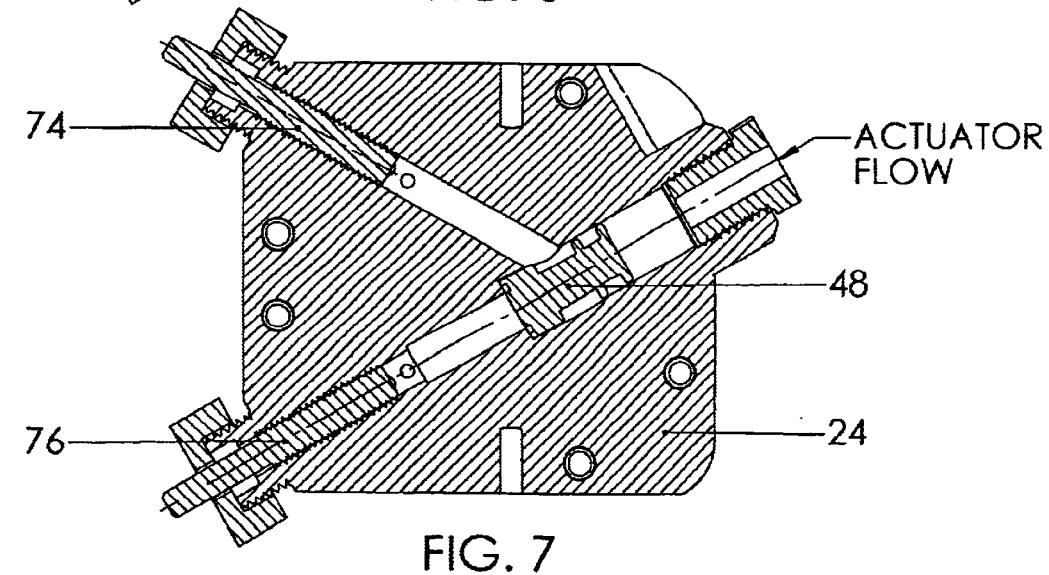
FIG. 7 is a cross section view through the control valve body in an active condition.

FIGS. 6 and 7 respectively depict the inactive and active states of the poppet valve 48. FIG. 6 and also FIG. 5 depict the inactive state when fluid flow through the control valve 24 is open to both the pistons 26 and 28 and which occurs when the piston chamber 47 and actuator piston 46 are floating in the control valve actuator 14. The "soft" piston 28 is selected during the inactive state by default, since the spring 30 offers the least resistance.

With appropriate deflection at the cams 58 and 60 and placement of a load on the pylon 8, the poppet valve 48 is shifted as shown at FIG. 7 due to the flow directed by the actuation piston 46. Fluid flow in the control valve 24 is then blocked to the cylinder containing the "soft" piston 28 and directed to the second stage cylinder containing piston 26 and the "hard" resistance spring 32, see also FIG. 4.

Needle valve assemblies 74 and 76 are provided at the control valve body 24 to permit an adjustment of the hydraulic fluid flow through the control valve body 24 and to the cylinders containing the "soft" and "hard pistons" 28 and 26. The needle valves 74 and 76 control the aperture size of ports in the fluid channels at the first and second stages and particularly control flexion and shock absorption over the gait of the wearer. The screw adjusters 34 and 36 correspondingly control the pre-compression and resistance of the springs 32 and 30.

Although the foregoing description is directed to a mechanical and hydraulic linkage to control movement of the knee assembly 10, other means and linkages, for example, other control valve actuator linkages and/or electronic sensors and drivers can provide a linkage to the cylinder 24 to operate the pistons 26 and 28. Still other multi-stage resistance devices, for example servomotors, might also be substituted for the two-stage cylinder 24 to provide counterbalancing and stabilizing forces at the prosthetic limb.

Figure 9:
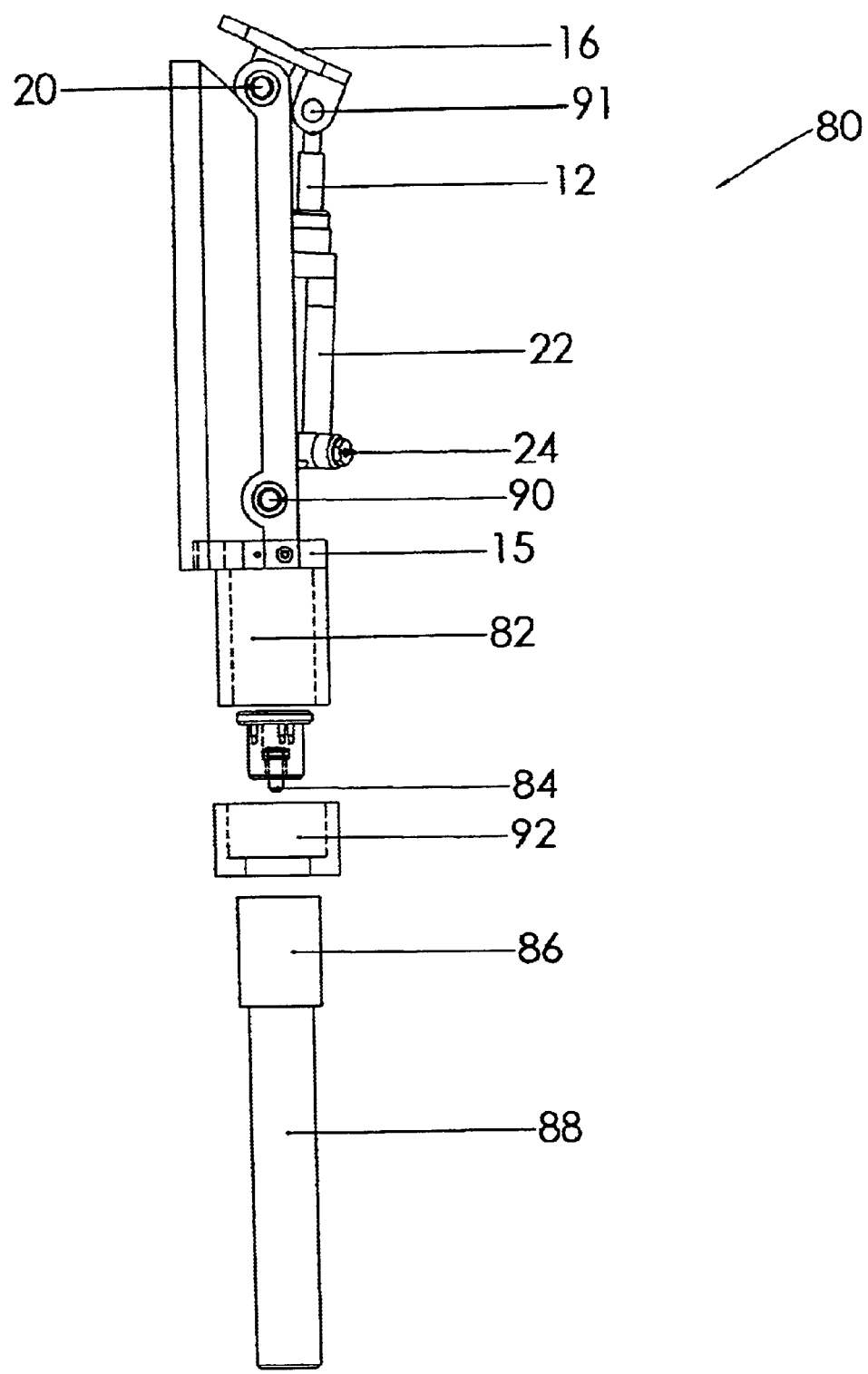
FIG. 9 is a plan view of an alternative knee joint assembly having a control valve, cylinder body, control valve actuator and interconnecting linkage.

FIG. 9 depicts an alternative prosthetic knee assembly 80 that is of a generally similar construction to the assembly 10. The principal difference exists at the control valve actuator 82 and wherein an actuator piston 84 is mounted to interact with a shaped head 86 of a splined pylon 88. As rotation is experienced in the knee 80 at the axle 20 and shafts 90 and 91, and with placement of weight onto the leg 2, the pylon 88 moves longitudinally in relation to a mounting nut 92 to induce movement of the actuator piston 84. The actuator piston 84 directs fluid flow to the cylinder 22 to control the poppet valve 48 and provide two different counter-balancing resistances to forces experienced by the leg 2.

Figure 10:
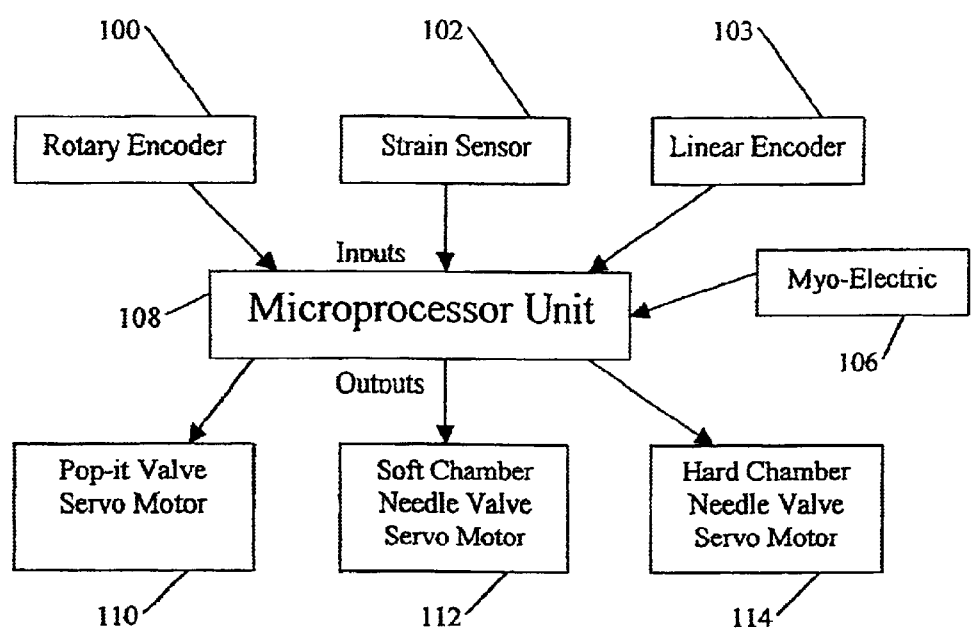
FIG. 10 is a block diagram showing several alternative leg/knee motion sensors and microprocessor directed hydraulic and servomotor controlled linkages that can be adapted to the improved knee joint assembly of the invention or other prosthetic limbs.

FIG. 10 depicts several alternative microprocessor-based control schemes that can be applied alone or in combination with the knee assemblies 10 or 80 or yet another knee assembly having servomotor-based joints. Various physical sensors such as a rotary encoder 100, linear encoder 103, strain sensor 102 and/or myoelectric sensor 106, shown in dashed line at FIG. 1, can be mounted to the knee assembly 10 to monitor and couple signals indicative of physical conditions to a microprocessor 108. Any myoelectric sensor could be coupled to appropriate nerves, for example at the socket 4. The rotary encoder 100 and linear encoder 102 could be coupled to the axle 20 and pylon 8 to detect and relative rotational and linear movement. Strain could be monitored between the cap piece 38 and the actuator body 14.

Depending upon the detected signals and comparisons to predetermined thresholds, tables or computed values, drive signals are applied via the microprocessor 108 and included driver circuitry to an appropriate servo. The servo can comprise a solenoid or servomotor, such as a pulse width modulated motor. A solenoid or servomotor 110 can be coupled to control the poppet valve 48. A servomotor 112 can be coupled to control the needle valve 74 and/or adjuster 36 to the soft piston 28. Another servomotor 114 can be coupled to control the needle valve 76 and/or adjuster 34 to the hard piston 26. The servos 112 and 114 can also be modulated during a stride to not only respond to encountered forces but also to store energy. Under any control scheme, however, the action of the servos 110–114 control the relative movement of the yokes 16 and 18 and/or pylon 8.

While the invention has been described with respect to a preferred construction and considered improvements or alternatives thereto, still other constructions may be suggested to those skilled in the art. That is, a variety of other means (mechanical or electrical or combinations thereof) can be adapted to activate a gait controlling and/or shock absorbing resistance device at a limb joint. Multiple levels of counter-resistance can be obtained by providing multiple resistance stages to provide an improved lifestyle to the user. The disclosed features of the invention might also be combined in different arrangements and with still other features in prosthetic assemblies for other limbs. The description therefore should not be literally construed in limitation of the invention. The foregoing description should instead be construed to include all those embodiments within the spirit and scope of the following claims.

What is claimed is:

1. A prosthetic knee comprising:

a) an axle and first and second yokes and wherein said first and second yokes are coupled to rotate relative to one another and at least one of said first and second yokes is coupled to rotate about said axle;

b) a hydraulic cylinder having first, second and third chambers mounted to one of said first and second yokes, wherein said first and second chambers include first and second springs mounted to bias first and second pistons to resist fluid flow directed against said first and second pistons by a plunger piston mounted in said third chamber and coupled to said axle;

c) a control valve body having a fluid flow channel coupled to said hydraulic cylinder and including a control member mounted in a fluid path to said hydraulic cylinder to divert fluid flow from said third chamber to a selected one of said first and second chambers to resist movement of said plunger piston; and d) an actuator coupled to said control valve body and responsive to external forces applied to one of said first and second yokes for manipulating said control member relative to external forces experienced by said knee.

2. A prosthetic knee as set forth in claim 1 including a cam mounted to one of said first and second yokes and a push rod mounted to the other of said first and second yokes and wherein said push rod is coupled to said actuator.

3. A prosthetic knee as set forth in claim 2 wherein said actuator comprises first and second pieces displaced from one another and mounted for reciprocating linear motion relative to one another in opposition to longitudinal forces experienced by said first and second yokes, wherein one of said first and second pieces contains an actuator piston, and wherein when one of said first and second yokes rotates a predetermined angular displacement, said push rod directs said actuator piston to manipulate said control member.

4. A prosthetic knee as set forth in claim 2 in combination with means coupled to one of said first and second yokes for mounting to a leg stump, wherein a prosthetic foot and a pylon are coupled to the other of said first and second yokes, wherein said actuator is coupled to said pylon and comprises an actuator body that includes an actuator piston, and wherein said push rod is coupled to said actuator body to induce said actuator piston to direct fluid to manipulate said control member.

5. A prosthetic knee as set forth in claim 4 wherein said actuator comprises first and second pieces displaced from one another and mounted for reciprocating linear motion relative to one another in opposition to longitudinal forces directed from said foot to said pylon and to said first and second yokes, wherein said actuator piston is mounted in a piston chamber in a cylinder of said actuator body, and wherein when one of said first and second yokes rotates a predetermined angular displacement, said push rod directs said actuator piston to manipulate said control member.

6. A prosthetic knee as set forth in claim 1 wherein said first and second springs exhibit different spring constants.

7. A prosthetic knee as set forth in claim 6 including means for adjusting the compression of at least one of said first and second springs.

8. A prosthetic knee as set forth in claim 7 wherein said control valve body includes a needle valve in said fluid flow channel for selectively controlling fluid flow therethrough.

9. A prosthetic knee as set forth in claim 1 wherein said actuator comprises an actuator body that includes an actuator piston, wherein a pylon is mounted to said actuator body to permit reciprocating movement relative to said actuator piston and such that when one of said first and second yokes rotates a predetermined angular displacement, said pylon directs said actuator piston to manipulate said control member.

10. A prosthetic knee as set forth in claim 1 wherein said actuator includes a servo and means for sensing myo-electric signals at a leg stump and means responsive to said myo-electric signals for directing said servo to manipulate said control member.

11. A prosthetic knee as set forth in claim 1 wherein said actuator includes a servo and means for sensing rotational movement at said knee and responsively coupling drive signals to said servo to manipulate said control member.

12. A prosthetic knee as set forth in claim 1 wherein said actuator includes a servo and means for sensing linear movement at said knee and responsively coupling drive signals to said servo to manipulate said control member.

13. A prosthetic knee as set forth in claim 1 wherein said actuator comprises an actuator body, a pylon mounted to said actuator body and a prosthetic foot coupled to said pylon and wherein said actuator includes a servo and means for sensing strain at said pylon and responsively coupling drive signals to said servo to manipulate said control member.

14. A prosthetic knee comprising:

a) an axle and first and second yokes and wherein said first and second yokes are coupled to rotate about said axle;

b) a hydraulic cylinder having first, second and third chambers mounted to one of said first and second yokes, wherein said first and second chambers include first and second springs mounted to bias first and second pistons to resist fluid flow directed against said first and second pistons by a plunger piston coupled to said axle and mounted in said third chamber;

c) a control valve body having a fluid flow channel coupled to said hydraulic cylinder and including a control member mounted in a fluid path to said hydraulic cylinder to divert fluid flow from said third chamber to a selected one of said first and second chambers to resist movement of said plunger piston;

d) an actuator coupled to said control valve body and responsive to external forces applied to said first and second yokes for manipulating said control member relative said external forces and comprising first and second pieces displaced from one another and mounted for reciprocating motion relative to one another; and e) a cam mounted to one of said first and second yokes and a linkage coupling said cam to said actuator, such that when one of said first and second yokes rotates a predetermined angular displacement said linkage directs said actuator to manipulate said control member.

15. A prosthetic knee as set forth in claim 14 in combination with means coupled to one of said first and second yokes for mounting to a leg stump, wherein a prosthetic foot and a pylon are coupled to the other of said first and second yokes, wherein said actuator is coupled to said pylon and comprises an actuator body that includes an actuator piston, and wherein said cam is mounted to a push rod linkage coupled to said actuator piston.

16. A prosthetic knee as set forth in claim 14 wherein said first and second springs exhibit different spring constants.

17. A prosthetic knee as set forth in claim 14 including means for adjusting the compression of at least one of said first and second springs.

18. A prosthetic knee as set forth in claim 14 wherein said control valve body includes a needle valve in said fluid flow channel for selectively varying the dimensions of said flow channel.

19. A prosthetic leg comprising:

a) a prosthetic knee including, 1) an axle and first and second yokes and wherein said first and second yokes are coupled to rotate about said axle;

2) a hydraulic cylinder having first, second and third chambers mounted to one of said first and second yokes, wherein said first and second chambers include first and second springs mounted to bias first and second pistons to resist fluid flow directed against said first and second pistons by a plunger piston coupled to said axle and mounted in said third chamber;

3) a control valve body coupled to said hydraulic cylinder and including a control member mounted in a fluid path between said hydraulic cylinder and said control valve body for diverting fluid flow from said third cylinder to a selected one of said first and second chambers to resist movement of said plunger piston;

4) an actuator coupled to said control valve body and responsive to external forces applied to said first and second yokes for manipulating said control member relative said external forces and comprising first and second pieces displaced from one another and mounted to accommodate reciprocating motion relative to one another and wherein one of said pieces includes an actuator piston; and 5) a cam mounted to one of said first and second yokes and a linkage responsive to movement of said cam coupled to said actuator, and wherein when said first and second yokes rotate to a predetermined relative angular relationship and when a predetermined displacement condition exists between said first and second actuator pieces said linkage directs movement of said actuator piston and thereby movement of said control member;

b) means coupled to one of said first and second yokes for mounting to a leg stump; and c) a prosthetic foot and a pylon coupled to said prosthetic foot and to said actuator.

20. A prosthetic knee as set forth in claim 19 wherein said first and second springs exhibit different spring constants.

* * * * *